United States Patent
Hibner et al.

(10) Patent No.: US 12,161,356 B2
(45) Date of Patent: Dec. 10, 2024

(54) SURGICAL INSTRUMENT WITH MULTI-FUNCTION BUTTON

(71) Applicant: Cilag GmbH International, Zug (CH)

(72) Inventors: John A. Hibner, Mason, OH (US); Kevin L Houser, Springboro, OH (US); David A. Monroe, Milford, OH (US); David J. Cagle, Cincinnati, OH (US); Geoffrey S. Strobl, Williamsburg, OH (US); Timothy P. Lessek, Mason, OH (US); Jeffrey L. Aldridge, Lebanon, OH (US); Ryan M. Asher, Cincinnati, OH (US); Mary E. Mootoo, Cincinnati, OH (US); Eric B. Smith, Cincinnati, OH (US); Gregory W. Johnson, Minneapolis, MN (US); David M. Locke, Springboro, OH (US)

(73) Assignee: Cilag GmbH International, Zug (CH)

( * ) Notice: Subject to any disclaimer, the term of this patent is extended or adjusted under 35 U.S.C. 154(b) by 140 days.

(21) Appl. No.: 17/725,022

(22) Filed: Apr. 20, 2022

(65) Prior Publication Data
US 2022/0313305 A1    Oct. 6, 2022

Related U.S. Application Data

(63) Continuation of application No. 16/266,578, filed on Feb. 4, 2019, now Pat. No. 11,452,539, which is a
(Continued)

(51) Int. Cl.
*A61B 17/32*    (2006.01)
*A61B 18/14*    (2006.01)
(Continued)

(52) U.S. Cl.
CPC .............. *A61B 17/320068* (2013.01); *A61B 17/320092* (2013.01); *A61B 18/1445* (2013.01);
(Continued)

(58) Field of Classification Search
CPC .... A61B 17/320068; A61B 17/320092; A61B 18/1445; A61B 2017/00451
See application file for complete search history.

(56) References Cited

U.S. PATENT DOCUMENTS 2,863,010 A    12/1958    Riedl
4,520,894 A    6/1985    Hensler
(Continued)

FOREIGN PATENT DOCUMENTS

CN    101011291 A    8/2007
CN    102512240 A    6/2012
(Continued)

OTHER PUBLICATIONS

Brazil Office Action dated Jun. 18, 2020, for Application No. BR112018012135-5, 4 pages.
(Continued)

*Primary Examiner* — Kathleen S Holwerda
(74) *Attorney, Agent, or Firm* — Frost Brown Todd LLP

(57) ABSTRACT

An ultrasonic instrument includes a body, an actuation assembly, a shaft assembly, and an end effector. The actuation assembly includes an activation member that is operable to move in a first direction to select a mode of operation. The shaft assembly extends distally from the body and includes an acoustic waveguide. The end effector includes an ultrasonic blade that is in acoustic communication with the acoustic waveguide. The activation member is operable to
(Continued)

move in a second direction to activate the end effector in a mode of operation selected by movement of the activation member in the first direction.

18 Claims, 10 Drawing Sheets

Related U.S. Application Data continuation of application No. 14/970,632, filed on Dec. 16, 2015, now Pat. No. 10,238,413.

(51) Int. Cl.
*A61B 17/00* (2006.01)
*A61B 18/00* (2006.01)

(52) U.S. Cl.
CPC ............... *A61B 2017/00389* (2013.01); *A61B 2017/00393* (2013.01); *A61B 2017/00407* (2013.01); *A61B 2017/0042* (2013.01); *A61B 2017/00446* (2013.01); *A61B 2017/00451* (2013.01); *A61B 2017/320071* (2017.08); *A61B 2017/320094* (2017.08); *A61B 2017/320095* (2017.08); *A61B 2018/00916* (2013.01); *A61B 2018/00922* (2013.01); *A61B 2018/00946* (2013.01); *A61B 2018/00952* (2013.01); *A61B 2018/00994* (2013.01)

(56) References Cited

U.S. PATENT DOCUMENTS

| | | | |
|---|---|---|---|
| 4,931,047 A | 6/1990 | Broadwin et al. | |
| 5,322,055 A | 6/1994 | Davison et al. | |
| 5,324,299 A | 6/1994 | Davison et al. | |
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,608,039 B1 | 10/2009 | Todd | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,663,220 B2 | 5/2014 | Wiener et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 10,238,413 B2 | 3/2019 | Hibner et al. | |
| 11,452,539 B2 | 9/2022 | Hibner et al. | |
| 2003/0176778 A1 | 9/2003 | Messing et al. | |
| 2004/0094597 A1 | 5/2004 | Whitman et al. | |
| 2004/0147947 A1* | 7/2004 | Donofrio | H01H 9/04 606/159 |
| 2006/0079874 A1 | 4/2006 | Faller et al. | |
| 2007/0011713 A1 | 1/2007 | Abramson et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0076504 A1 | 3/2009 | Schnitzler | |
| 2010/0069940 A1* | 3/2010 | Miller | A61B 17/320068 606/169 |
| 2010/0274160 A1* | 10/2010 | Yachi | H01H 13/08 606/1 |
| 2011/0015627 A1 | 1/2011 | DiNardo et al. | |
| 2012/0112687 A1 | 5/2012 | Houser et al. | |
| 2012/0116265 A1 | 5/2012 | Houser et al. | |
| 2013/0282003 A1 | 10/2013 | Messerly et al. | |
| 2014/0005701 A1 | 1/2014 | Olson et al. | |
| 2014/0135804 A1 | 5/2014 | Weisenburgh et al. | |
| 2014/0155921 A1 | 6/2014 | Price et al. | |
| 2015/0066026 A1* | 3/2015 | Hart | A61B 34/76 606/46 |
| 2015/0080924 A1 | 3/2015 | Stulen et al. | |
| 2015/0141981 A1 | 5/2015 | Price et al. | |
| 2015/0142033 A1 | 5/2015 | Stulen et al. | |

FOREIGN PATENT DOCUMENTS

| | | |
|---|---|---|
| CN | 102647949 A | 8/2012 |
| CN | 102879894 A | 1/2013 |
| CN | 104363843 A | 2/2015 |
| CN | 105012012 A | 11/2015 |
| EP | 2455007 A2 | 5/2012 |
| EP | 2772206 A2 | 9/2014 |
| JP | 2000-287986 A | 10/2000 |
| JP | 2007-275291 A | 10/2007 |
| JP | 2011-143252 A | 7/2011 |
| WO | WO 2011/121827 A1 | 10/2011 |
| WO | WO 2015/077139 A1 | 5/2015 |

OTHER PUBLICATIONS

Chinese First Office Action and Search Report dated Jul. 3, 2020, for Application No. 201680074011.1, 13 pages.
Chinese Second Office Action dated Mar. 16, 2021, for Application No. 201680074011.1, 15 pages.
European Communication dated Apr. 9, 2021, for Application No. 16828819.9, 6 pages.
European Communication dated Dec. 15, 2021, for Application No. 16828819.9, 5 pages.
Indian Office Action dated Aug. 19, 2021, for Application No. 201817019938, 5 pages.
International Search Report and Written Opinion dated Apr. 7, 2017, for International Application No. PCT/US2016/066461, 12 pages.
International Preliminary Report on Patentability dated Jun. 19, 2018, for International Application No. PCT/US2016/066461, 8 pages.
Japanese Notification of Reasons for Refusal dated Dec. 1, 2020, for Application No. 2018-531328, 8 pages.
U.S. Appl. No. 61/410,603, entitled "Energy-Based Surgical Instruments," filed Nov. 5, 2010.

\* cited by examiner

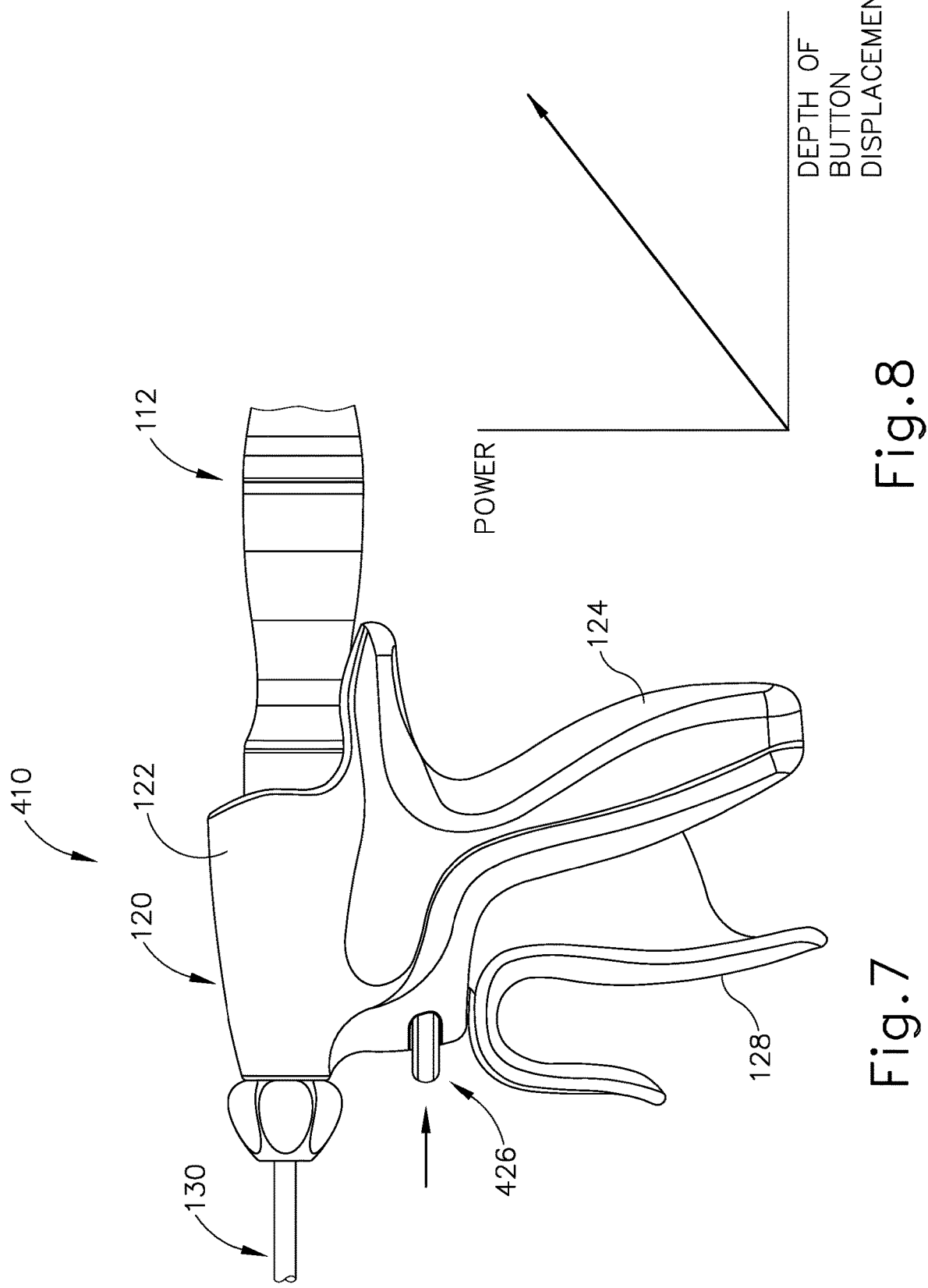

SURGICAL INSTRUMENT WITH MULTI-FUNCTION BUTTON

This patent application is a continuation of U.S. patent application Ser. No. 16/266,578, entitled "Surgical Instrument with Multi-Function Button" filed on Feb. 4, 2019, now U.S. Pat. No. 11,452,539 issued Sep. 27, 2022, which is a continuation of U.S. patent application Ser. No. 14/970,632, entitled "Surgical Instrument with Multi-Function Button" filed on Dec. 16, 2015, now U.S. Pat. No. 10,238,413 issued Mar. 26, 2019, the entire disclosures of which are expressly incorporated herein by reference.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,39,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts a side elevational view of another exemplary surgical instrument, including another exemplary alternative activation button;

FIG. 8 depicts a graph showing a plot of button displacement versus power associated with the surgical instrument of FIG. 7;

Figure 1:
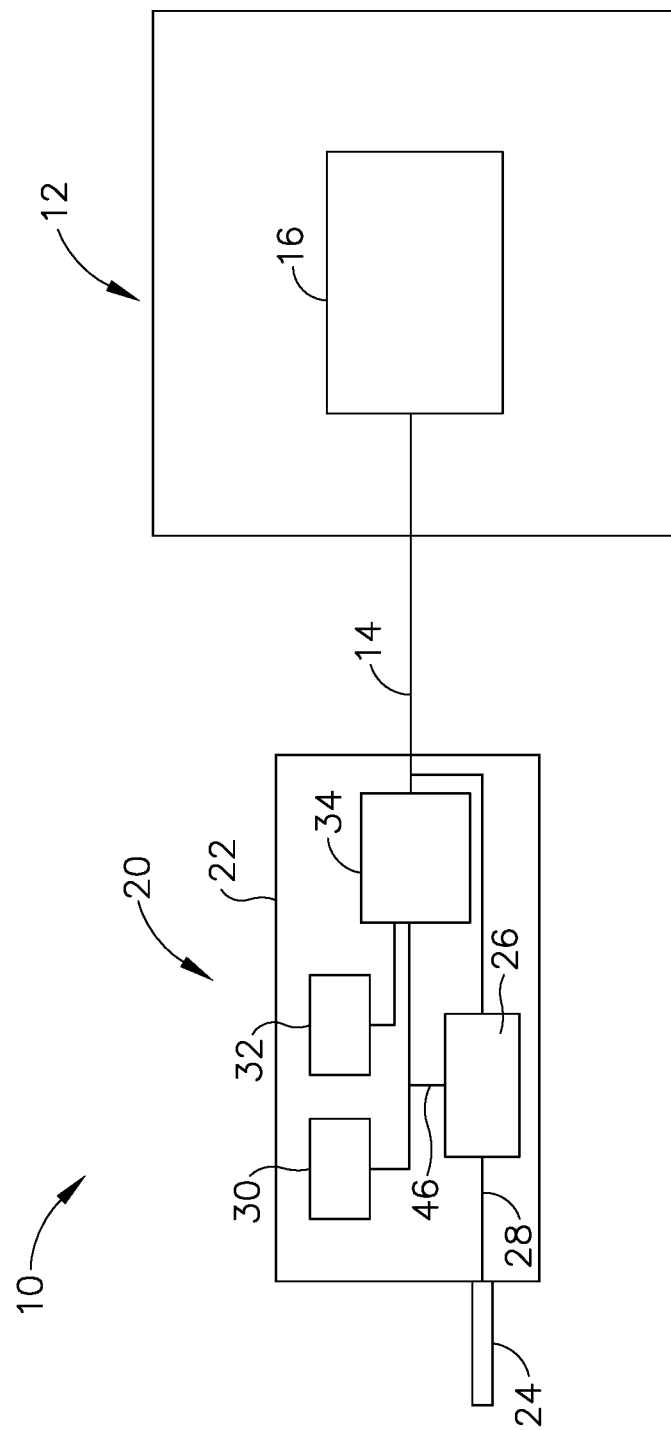
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. OVERVIEW OF EXEMPLARY ULTRASONIC SURGICAL SYSTEM

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_0$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_0$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. OVERVIEW OF EXEMPLARY ULTRASONIC SURGICAL INSTRUMENT

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

In some instances it may be advantageous to include a variety of functionalities in a single surgical instrument. For example, when using ultrasonic surgical instruments, it may be useful in some instances to deliver varying levels of power or energy to tissue. Particularly, some instances may call for both cutting and sealing of tissue, but other instances may call for only sealing of tissue. Levels of energy and/or power that may be applied in a "seal" mode and in a "cut and seal" mode will be apparent to persons skilled in the art in view of the teachings herein. While increasing the functionality of a surgical instrument to operate in a variety of modes may be advantageous, doing so may lead to an increased number of buttons, switches, and other control mechanisms that an operator must understand and utilize. Therefore, it is desirable to provide increased functionality of surgical instruments without increasing the complexity of use. The following examples provide enhanced control of power modes in variations of instrument (20), without providing an unduly complex user interface.

A. Instrument Including Sensor for Detecting Characteristics of Operator

Figure 2:
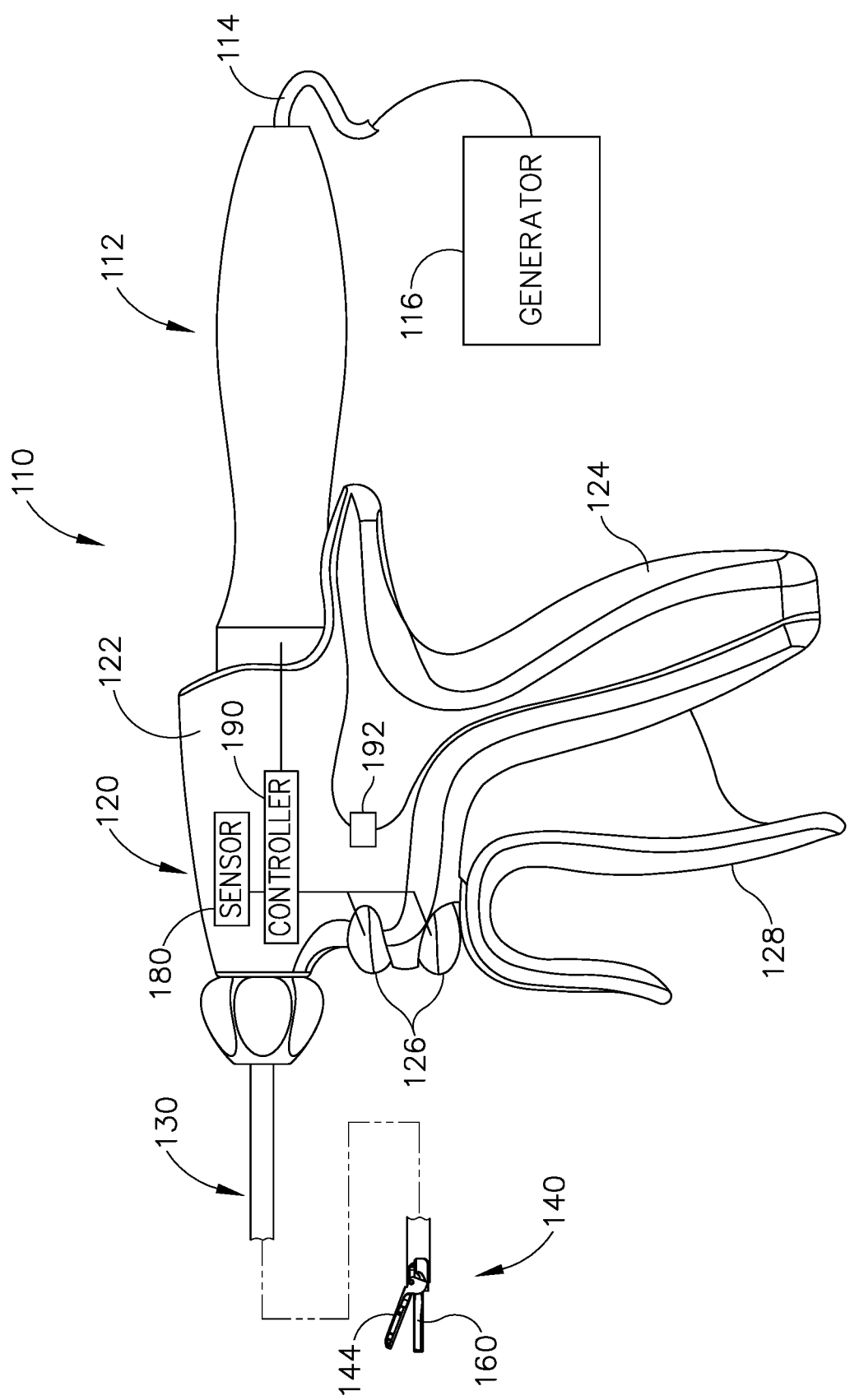
FIG. 2 depicts a side elevational view of another exemplary surgical instrument, including a sensor.

FIG. 2 illustrates an exemplary ultrasonic surgical instrument (110). At least part of instrument (110) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (120) is operable to cut tissue and seal or weld tissue substantially simultaneously. It should also be understood that instrument (120) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (120) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (120), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (22) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Clamp arm (144) is thus operable to cooperate with ultrasonic blade (160) to grasp and release tissue; and clamp arm (144) is further operable to compress tissue against ultrasonic blade (160) to thereby enhance the communication of ultrasonic vibration from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (136) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (44) and blade (160). In particular, activation of a second one of the buttons (136) may cause vibration of ultrasonic blade (160) at a relatively high amplitude. Other suitable operational modes that may be associated with buttons (126) will be apparent to persons skilled in the art in view of the teachings herein.

Still referring to FIG. 2, operational modes associated with buttons (126) may change depending on certain characteristics sensed by instrument (110). In the present example, instrument (110) includes a sensor (180) that is configured to sense whether the operator is left-handed or right handed. Particularly, in the present example, sensor (180) is configured to detect or determine if the operator is holding instrument (110) in the operator's left hand or right hand by using one or more various suitable sensing modalities. Suitable sensing modalities include, but are not limited to inductive, capacitive, resistive, thermal, reflective, pressure, density, infrared/heat, lateral trigger load, lateral trigger deflection, accelerometer sensing during trigger closure, and various other suitable sensing modalities that will be apparent to persons skilled in the art in view of the teachings herein. Various suitable ways in which such sensing modalities may be incorporated into instrument (110), and various suitable ways in which such sensing modalities may be used to sense whether the operator is grasping handle assembly (120) in the operator's left hand or the operator's right hand, will be apparent to those of ordinary skill in the art in view of the teachings herein.

While one sensor (180) is shown in the present example, other versions may include various sensors of the same or different types. Moreover, it will be understood that sensor (180) may be positioned in handle assembly (120), for example, according to which sensing modality is utilized. In some examples, however, sensor (180) may be positioned in a different portion of instrument (110), such as shaft assembly (130), end effector (140), and/or other suitable parts of instrument (110). In some examples, rather than buttons activating transducer (112), closure of trigger (128) may activate transducer (112). In such examples, sensor (180) may sense the angle of trigger (128) relative to particular components of instrument (110), such as, for example, pistol grip (124). In such examples where closure of trigger (128) initiates activation of transducer (112), the prevention of early or unintended activation of transducer (112) may be prevented. Other suitable methods for activating transducer (112) will be apparent to persons skilled in the art in view of the teachings herein.

As shown, sensor (180) is in communication with a controller (190) which, in response to receiving sensed/detected information from sensor (180), may communicate to buttons (126), transducer (112), and/or other components of instrument (110) the operational modes under which instrument (110) should operate upon actuation of buttons (126). For example, upon sensing that the operator is grasping handle assembly (120) with a particular hand, sensor (180) and controller (190) communicate to instrument (110) that actuation of one of buttons (126) should activate transducer (112) and blade (160) in a first operational mode while actuation of the other of the buttons (126) should activate transducer (112) and blade (160) in a second operational mode.

In addition to buttons (126), instrument (110) of the present example further includes a button (192) on each side of handle assembly (120). Such buttons (192) are positioned such that one of the buttons (192) may be engaged by the thumb of the hand that grasps pistol grip (124), the particular button (192) depending on which hand the operator uses to grasp pistol grip (124). While button (192) is shown on one side of handle assembly (120), it will be understood that another button (192) is positioned on the other side of handle assembly (120) that is not shown. In some versions, buttons (192) are operable to activate transducer (112) to drive blade (160) to vibrate at an ultrasonic frequency. In some such versions, one or both of buttons (126) is/are omitted. For instance, the single button (126) may provide ultrasonic energy at one power level while the other button (192) may provide ultrasonic energy at another power level. In some other versions, buttons (192) are operable to activate features that are configured to apply RF electrosurgical energy to tissue via end effector (140). By way of example only, buttons (192) may be configured and operable in accordance with at least some of the teachings of U.S. Pub. No. 2015/0141981, entitled "Ultrasonic Surgical Instrument with Electrosurgical Feature," published May 21, 2015, now U.S. Pat. No. 9,949,785, issued Apr. 24, 2018, the disclosure of which is incorporated by reference herein. By way of further example only, end effector (140) may incorporate RF electrosurgical functionality in accordance with at least some of the teachings of U.S. Pat. No. 8,663,220, entitled "Ultrasonic Surgical Instruments," issued Mar. 4, 2014, the disclosure of which is incorporated by reference herein. Other suitable functionalities that may be tied to buttons (192), and other suitable ways in which end effector (140) may incorporate RF electrosurgical functionality, will be apparent to those of ordinary skill in the art in view of the teachings herein.

In the present example, controller (190) is configured to selectively enable one button (192) while disabling the other button (192) based on which hand the operator uses to grasp handle assembly (120), as detected by sensor (180). For example, upon detecting that the operator is grasping handle assembly (120) in the operator's left hand, controller (190) may enable the button (192) on the right side of handle assembly (120) (i.e., where the operator's left thumb would be located) and disable the button (192) on the left side of handle assembly (120). Thus, if the operator who grasps handle assembly (120) in the operator's left hand actuates the button (192) on the right side of handle assembly (120), the actuation of the right side button (192) will trigger ultrasonic vibration of blade (160) and/or application of RF energy to tissue via end effector (140). If the same operator who grasps handle assembly (120) in the operator's left hand incidentally actuates the button (192) on the left side of handle assembly (120), the actuation of the left side button (192) will have no effect.

Conversely, if an operator who grasps handle assembly (120) in the operator's right hand actuates the button (192) on the left side of handle assembly (120) (i.e., where the operator's right thumb would be located), the actuation of the left side button (192) will trigger ultrasonic vibration of blade (160) and/or application of RF energy to tissue via end effector (140). If the same operator who grasps handle assembly (120) in the operator's right hand incidentally actuates the button (192) on the right side of handle assembly (120), the actuation of the right side button (192) will have no effect.

As another merely illustrative variation, controller (190) may still enable both buttons (192) during operation of instrument (110), yet provide different functionality in response to actuation of each button (192) based on the hand that the operator uses to grasp handle assembly (120). For instance, when the operator grasps handle assembly (120) with the operator's left hand, controller (190) may provide a first functionality in response to actuation of the left side button (192) and a second functionality in response to actuation of the right side button (192). Other suitable operational modes under which instrument (110) may operate in response to data sensed by sensor (180), and other responses that instrument (110) may provide based on data sensed by sensor (180), will be apparent to persons skilled in the art in view of the teachings herein.

B. Surgical Instrument with Multi-Position Toggle Activation Button

Figure 3:
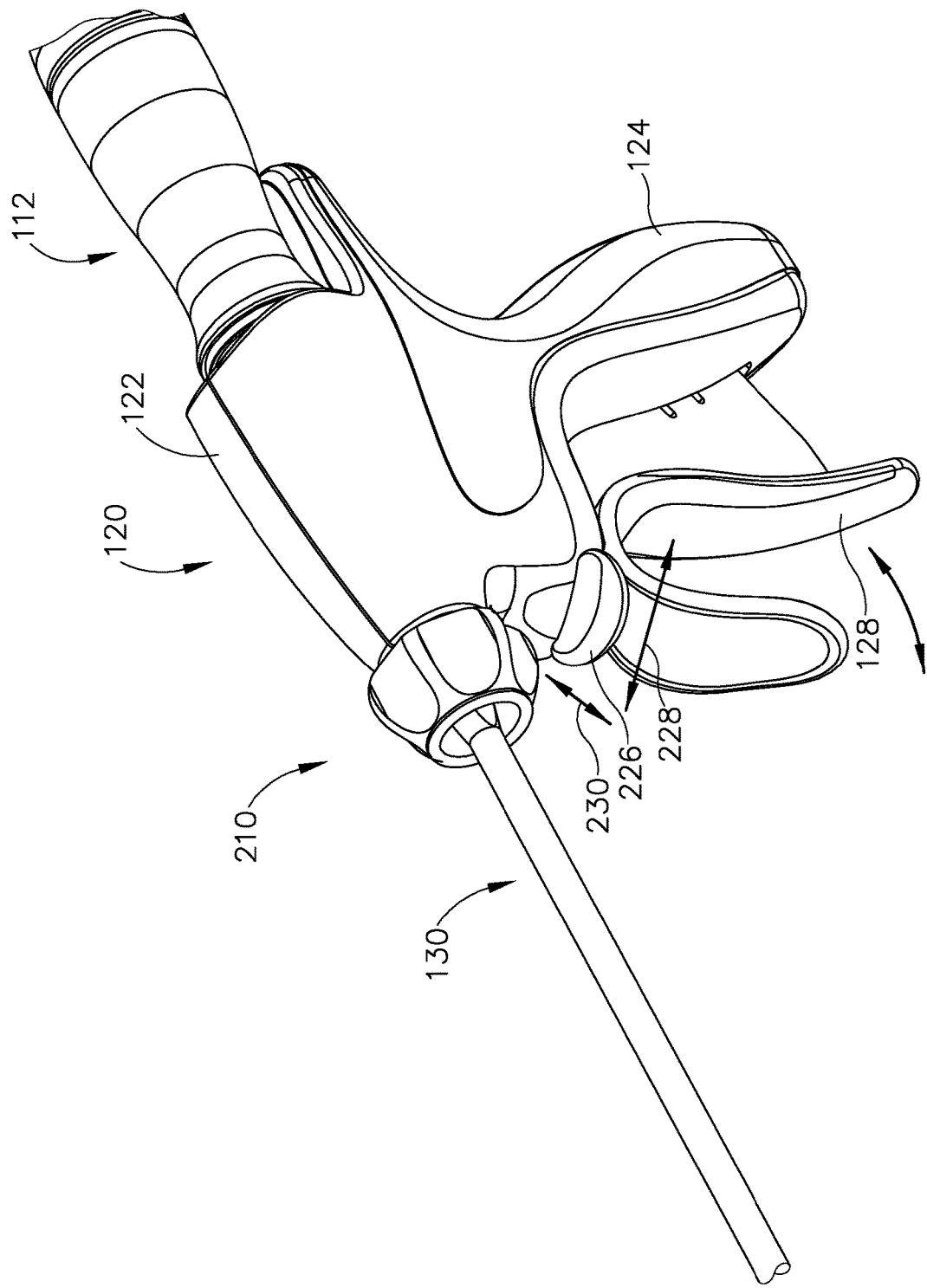
FIG. 3 depicts a perspective view of another exemplary surgical instrument including an exemplary alternative activation button.
Figure 4A:
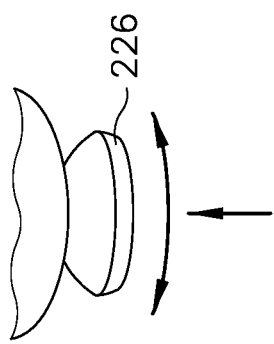
FIG. 4A depicts a top schematic view of the activation button of the surgical instrument of FIG. 3, showing the activation button in a first position.
Figure 4B:
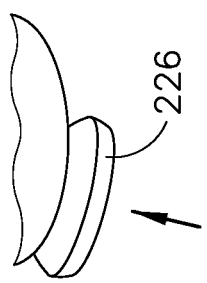
FIG. 4B depicts a top schematic view of the activation button of the surgical instrument of FIG. 3, showing the activation button in a second position.
Figure 4C:
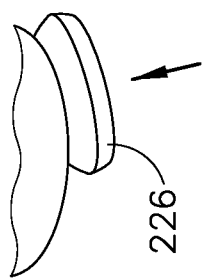
FIG. 4C depicts a top schematic view of the activation button of the surgical instrument of FIG. 3, showing the activation button in a third position.

FIGS. 3-4C show an exemplary alternative surgical instrument (210) that is configured to operate substantially similar to surgical instrument (110). Therefore, identical or similar structures are labeled with like reference numerals without further explanation below. It will be understood that although an end effector is not shown in FIG. 3, instrument (210) includes an end effector that is just like end effector (140) described above. It will be further understood that transducer (112) may be in communication with a generator (12, 116) via cable (14). Surgical instrument (210) of this example includes a single activation button (226) that is configured to transition between various positions. As discussed in detail below, instrument (210) is configured to operate in different operational modes, depending on the position of activation button (226) upon the actuation of activation button (226).

In the present example, button (226) is configured to toggle among three positions, each of which is associated with different operational modes. Once button (226) is positioned into one of the three positions (along bi-directional arrow (228)), button may be pressed or otherwise actuated (e.g., in the direction of arrow (230)) to activate transducer (112) and thereby activate blade (160). In the example shown, in the first position (FIG. 4A) button (226) is laterally centered. In the second position, as shown in FIG. 4B, button (226) has been pivoted in a first direction about an axis that is perpendicular to the longitudinal axis of instrument, such that button (226) is deflected to a first side of the laterally centered positioned. In the third position as shown in FIG. 4C, button (226) has been pivoted in a second direction (opposite of the first direction) about an axis that is perpendicular to the longitudinal axis of instrument (210), such that button (226) is deflected to a second side of the laterally centered positioned. While button (226) is shown as pivoting about an axis to transition between the first, second, and third positions, other versions may provide a purely lateral movement of button (226) (i.e., along a straight, linear path) to transition between first, second, and third positions.

In some versions, button (226) includes detent features that selectively maintain the position of button (226) in the position selected from the first, second, and third positions. Such detent features may provide some degree of resistance to movement between the first, second, and third positions (i.e., to prevent inadvertent movement between the first, second, and third positions); yet still permit intended movement between the first, second, and third positions. Various suitable forms that such detent features may take will be apparent to those of ordinary skill in the art in view of the teachings herein. In addition or in the alternative, button (226) may be resiliently biased toward the first position such that the operator must overcome the resilient bias in order to achieve the second or third positions. In some such versions, the operator must maintain a retention force in order to maintain the second or third position. Once the operator removes the retention force, button (226) will be resiliently urged back to the first position.

While button (226) is shown as being operable to transition between three positions, it will be understood that button (226) may be operable to assume more than three positions or less than three positions. While button (226) is shown to be rotated or pivoted along an axis that is perpendicular to the longitudinal axis of instrument (210) to be moved amongst the first, second, and third positions, it will be understood that button may be rotated about differently oriented axes and/or translated along different axes to assume a variety of positions associated with various operating modes. Other suitable configurations of button (226) will be apparent to persons skilled in the art in view of the teachings herein.

In the example shown, button (226) is not capable of activating transducer (112) and blade (160) when button (226) is in the first position. In some versions, instrument (210) includes a locking element that physically resists or impedes the actuation of button (226) from moving in the direction of arrow (230) when button (226) is in the first position. In some other versions, button (226) may be physically actuated in the direction of arrow (230) while button (226) is in the first position, but such actuation of button (226) in the first position does not result in activation of transducer (112) and blade (160). For instance, button (226) may be incapable of closing an activation circuit when button (226) is in the first position. In still other examples, button (226) will activate end effector (140) in a first operational mode (e.g., low ultrasonic energy, high ultrasonic energy, RF energy, etc.) when button (226) is actuated while button (226) is at the first position.

In the present example, actuation of button (226) in the second position activates transducer (112) and blade (160) at a first power level, while actuation of button (226) in the third position activates transducer (112) and blade (160) at a second power level. By way of example only, the first power level may provide the "seal" mode described above; while the second power level may provide the "cut and seal" mode described above. In other versions, the different positions of button (226) may be associated with other, different power levels or activation modes. Moreover, in addition or in the alternative to discrete positions of the button (226) being associated with particular operating modes, toggling the button in the first or second direction may change the power level in a continuous, linear manner, instead of a step-like manner. Various components and configurations that may be incorporated into instrument (210) in order to provide the above-described responses based on the position of button (226) will be apparent to those of ordinary skill in the art in view of the teachings herein.

C. Surgical Instrument with Adjustable, Scrolling Activation Button

Figure 5:
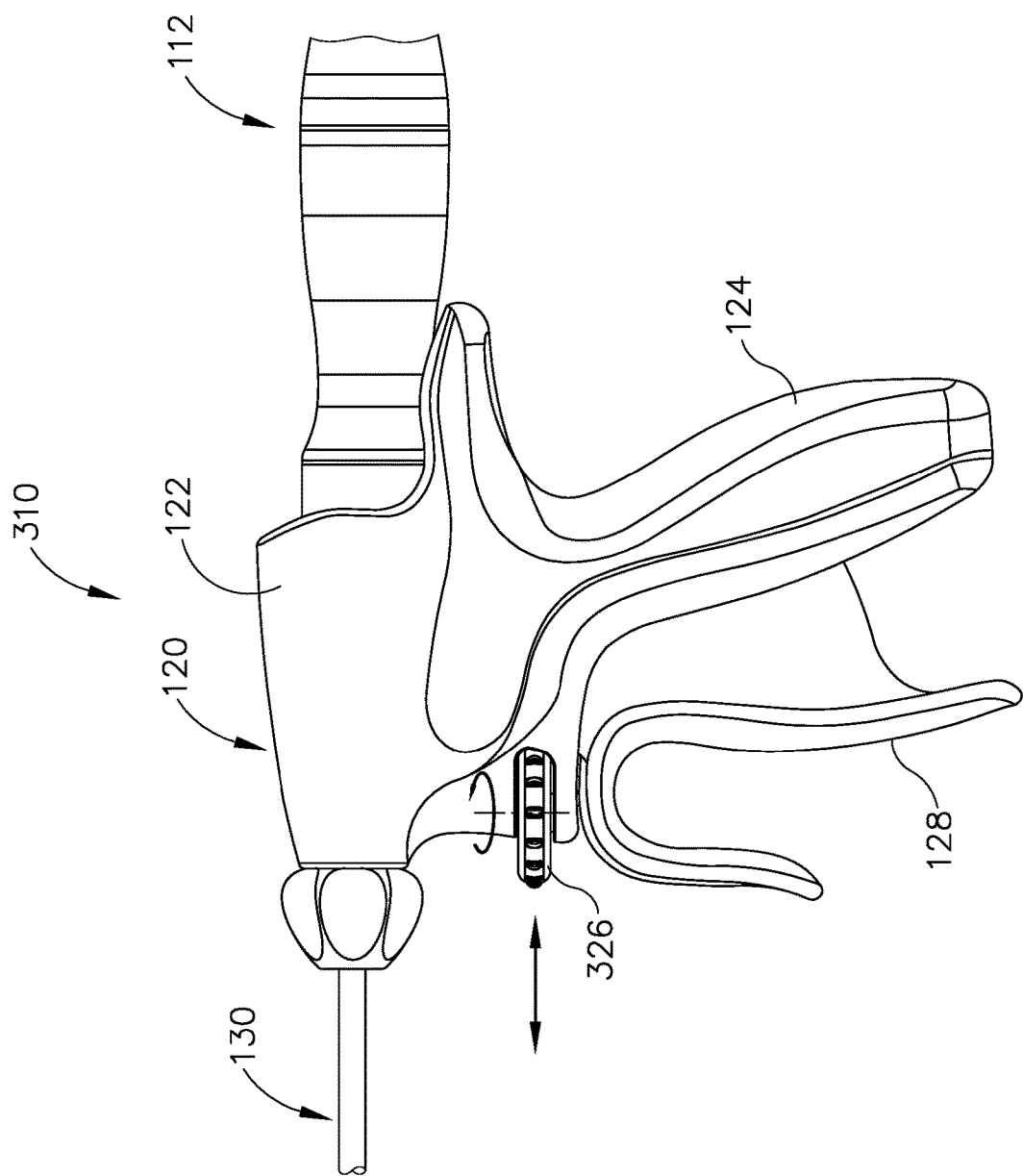
FIG. 5 depicts a side elevational view of another exemplary surgical instrument, including another exemplary alternative activation button.
Figure 6:
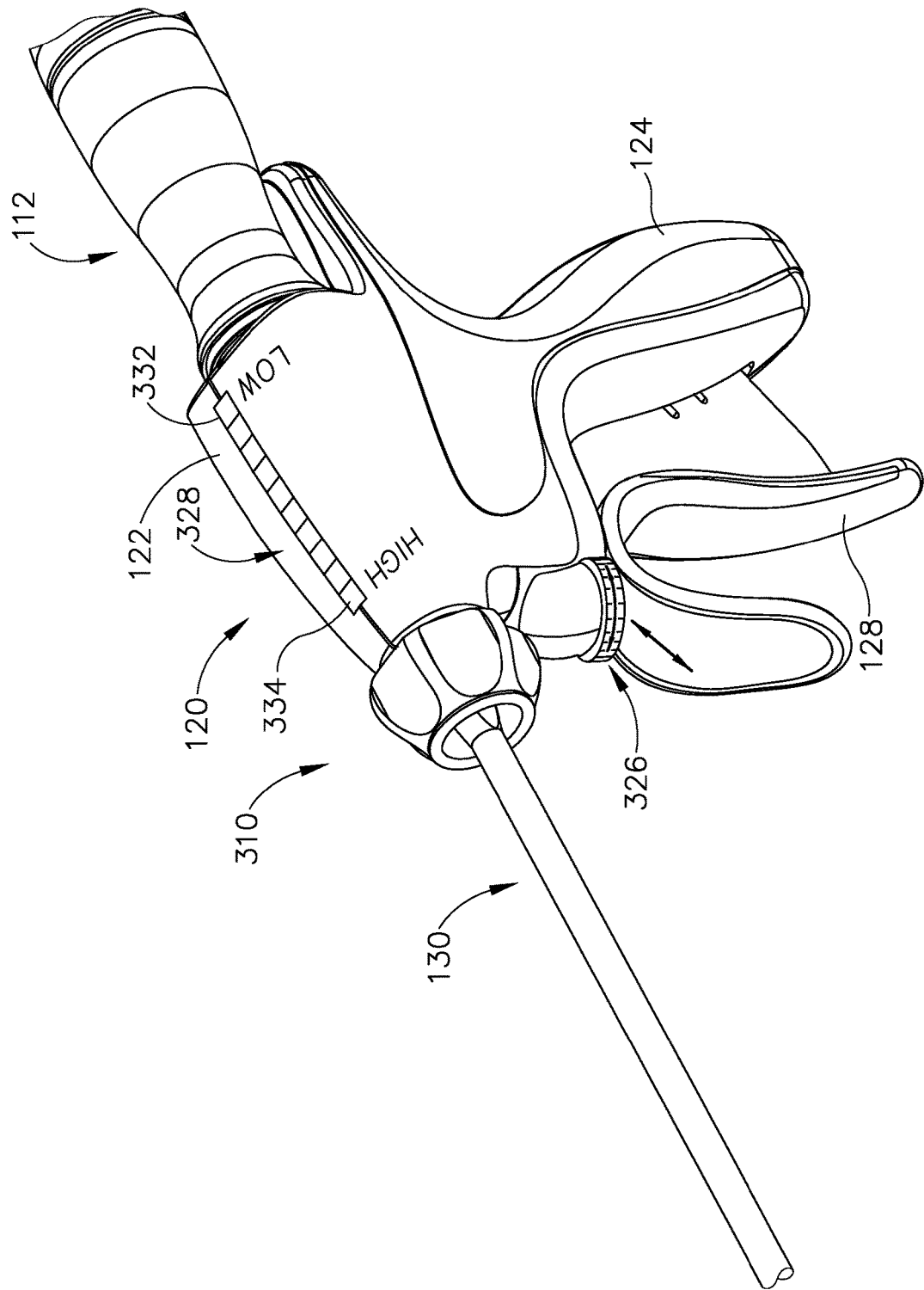
FIG. 6 depicts a perspective view of the surgical instrument of FIG. 5, showing a power display feature.

FIGS. 5-6 show an exemplary alternative surgical instrument (310) that is configured to operate substantially similar to surgical instrument (110). Therefore, identical or similar structures are labeled with like reference numerals without further explanation below. It will be understood that although an end effector is not shown in FIG. 4, instrument (310) includes an end effector that is just like end effector (140) described above. It will be further understood that transducer (112) may be in communication with a generator (12, 116) via cable (14). Surgical instrument (310) includes a single activation button (326), which is rotatable to select a power level or activation mode, which is shown on a power level display (328). Therefore, as discussed in detail below, instrument (310) is configured to operate in different operational modes, depending on the rotational position of activation button (326) upon the actuation of activation button (326).

Particularly, button (326) is rotatable about an axis that is perpendicular to a longitudinal axis of shaft assembly (130). In the example shown, rotating button (326) in a first direction (left as shown in FIG. 6) results in the power level increasing, while rotating button in a second direction (right as shown in FIG. 4) results in the power level decreasing. However, in other examples, rotation in the first direction may result in the power level decreasing and rotation in the second direction may result in the power level increasing. In the present example, button (326) is associated with a potentiometer that increases or decreases the power level linearly and continuously as button (326) is rotated in the first or second directions, respectively.

In some other examples, however, rotation of button (326) may result in step-wise increasing or decreasing among discrete power levels or operational modes. For example, rotation of button (326) in the first direction may increase the power level from zero, to a power level associated with the "seal" activation mode described above, to a power level associated with the "cut and seal" activation mode described above, and any suitable number of modes between zero and "seal," between "seal" and "cut and seal," and above "cut and seal." Similarly, rotation of button (326) in the second direction may decrease the power level from, for example, the power level associated with the "cut and seal" activation mode, to the "seal" activation mode, and to zero, and any suitable number of modes between "cut and seal" and "seal," and between "seal" and zero. Other suitable activation modes that may be provided according to the positioning of button (326) will be apparent to persons skilled in the art in view of the teachings herein. In versions where rotation of button (326) provides step-wise increasing or decreasing among discrete power levels or operational modes, detent features and/or other features may provide tactile and/or audible feedback to indicate to the operator that instrument (310) is transitioning between the discrete power levels or operational modes.

As shown, button (326) may be rotated until the maximum power level is reached upon which the button (326) is impeded from further rotation in the first direction. Similarly, button may be rotated in the second direction until the minimum power level (e.g., zero power) is reached. Various suitable mechanical or other manners of impeding the further rotation of button (326) will be apparent to persons skilled in the art in view of the teachings herein. In some examples, however, button (326) may continue to be rotated after the power level has reached the minimum and maximum. In such examples, instrument (310) may include any suitable electronic controls to prevent the power level from increasing above a predetermined maximum power level.

While button (326) is shown to be rotated about an axis that is perpendicular to the longitudinal axis of shaft assembly (130) to increase or decrease the power level, it will be understood that button (326) may be rotated along differently positioned axes to assume a variety of positions that are associated with a variety of power levels. Moreover, in some examples, rather than being rotated, button (326) may be translated (e.g. parallel, perpendicular, or oblique to longitudinal axis) in order to increase or decrease the power level.

Power level display (328) is configured to provide the operator with visual feedback indicating the power level selected by rotation of button (326). As shown, display (328) includes a proximal end (332) associated with a low power level and a distal end (334) associated with a high power level. In the present example, as the power level increases, different portions of display (328) are illuminated. For example, as the power level increases, more distal portions of display (328) are progressively illuminated. In some examples, display (328) includes colors associated with the power levels. In such examples, green and yellow colors may indicate a relatively lower power level, while orange and red may indicate relatively higher power level. By way of example only, display (328) may include a linear array of LEDs or other light sources. Other suitable components and configurations that may be used to provide display (328) will be apparent to persons skilled in the art in view of the teachings herein.

D. Surgical Instrument with Continuously Variable Activation Button

FIG. 7 shows an exemplary alternative surgical instrument (410) that is configured to operate substantially similar to surgical instrument (110). Therefore, identical or similar structures are labeled with like reference numerals without further explanation below. It will be understood that although an end effector is not shown in FIG. 7, instrument (410) includes an end effector just like end effector (140) described above. It will be further understood that transducer (112) may be in communication with a generator (12, 116) via cable (14). As shown, surgical instrument (410) includes a single activation button (426) that is configured to provide a continuously variable power level, rather than operating in discrete modes or power levels. Particularly, in the example shown, as the depth of proximal actuation of button (436) increases, the power level of transducer (112) and blade (160) increases.

In the present example, and as shown in FIG. 8, the power setting or displacement of ultrasonic blade (160) increases linearly as the depth of button (436) press increases. In some other examples, however, the power setting or displacement of ultrasonic blade (160) may increase at non-linear rate, such as step-wise, exponentially, etc. Other suitable relationships between the power setting or displacement of ultrasonic blade (160) and the depth or pressure of button (426) will be apparent to persons skilled in the art in view of the teachings herein. In some examples, the tension or physical resistance of button (436) may be varied across the throw (i.e., across the range of travel of button (436)) in order to provide the operator with tactile feedback and more control over the movement of button (436) and ultrasonic blade (160). Providing button (436) with a continuously variable power level enables the operator to operate across a continuum of modes (e.g., power levels) without being constrained to discrete settings (maximum, minimum, etc.).

E. Surgical Instrument with Multi-Function, Single Activation Button

Figure 9:
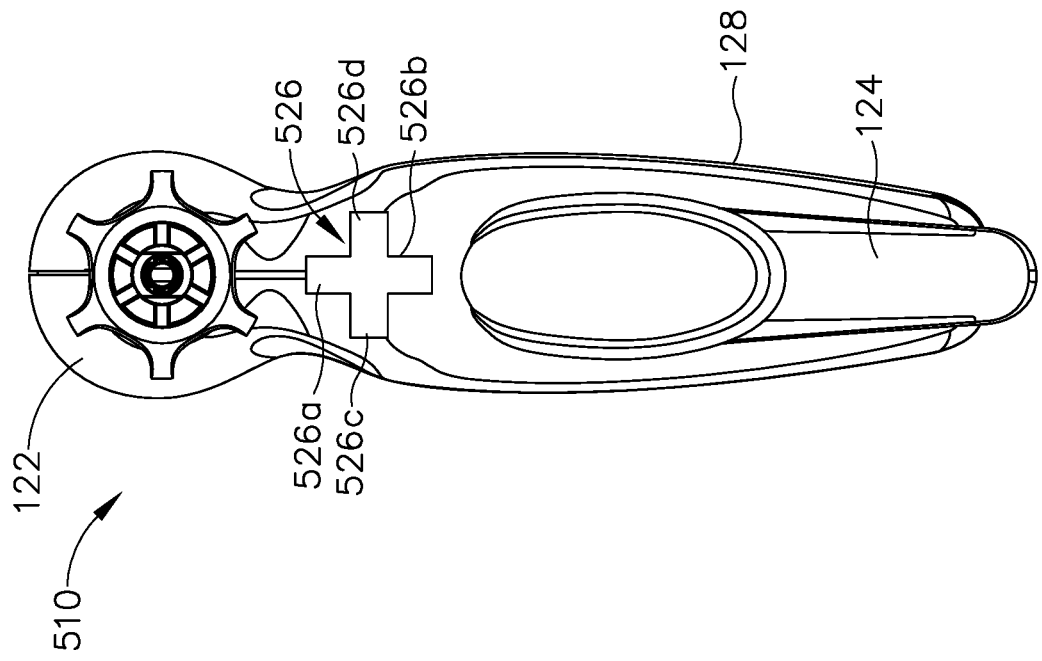
FIG. 9 depicts a front elevational view of another exemplary surgical instrument, including another exemplary alternative activation button.

FIG. 9 shows an exemplary alternative surgical instrument (510) that is configured to operate substantially similar to surgical instrument (110). Therefore, identical or similar structures are labeled with like reference numerals without further explanation below. It will be understood that although an end effector is not shown in FIG. 9, instrument (510) includes an end effector that is just like end effector (140). It will be further understood that transducer (112) may be in communication with a generator (12, 116) via cable (14).

As shown, instrument (510) includes a single activation button (526) having a plurality of switches associated with various operating modes. In the present example, button (526) is a multi-directional button having a first leg (526a), a second leg (526b), a third leg (526c), and a fourth leg (526d). Legs (526a, 526b, 526c, 526d) are perpendicular to each other and thereby define a "+" configuration. In some other versions, button (526) has a round shape or some other configuration. It should be understood that each leg (526a, 526b, 526c, 526d) may be pressed separately; or a pair of legs (526a, 526b, 526c, 526d) may be pressed simultaneously. When one or more legs are pressed (526a, 526b, 526c, 526d), button (526) will close one or more corresponding switches to thereby activate end effector (140) as described in greater detail below.

By way of example only, first leg (526a) may be associated with a "maximum" setting, second leg (526b) may be associated with a "minimum" setting, and third and fourth legs (526c, 526d) may be associated with a "hemostasis" setting. Levels of energy and/or power that may be applied in the "minimum," "maximum," and "hemostasis" modes will be apparent to persons skilled in the art in view of the teachings herein. It should also be understood that button (526) may be operable to provide selection from ultrasonic and RF power delivery modes. For instance, first and second legs (526a, 526b) may be operable to provide ultrasonic energy at end effector (140) at two different power levels; and third and fourth legs (526c, 526d) may be operable to provide RF energy at end effector (140) at two different power levels.

In the present example, button (526) includes four legs (526a, 526b, 526c, 526d) that allow for at least two operating modes. In versions where third and fourth legs (526c, 526d) each activate a "hemostasis" operating mode (or other operating mode), due to the opposing lateral positions of third and fourth legs (526c, 526d), a practitioner may easily utilize the "hemostasis" operating mode (or other operating mode) regardless of the operator's or her left-handedness or right-handedness. That is, third leg (526c) may be more easily accessible to a right-handed person than is fourth leg (526d). Similarly, fourth leg (526d) may be more easily accessible to a left-handed person than is third leg (526c). Due to the locations of first and second legs (526a, 526b) being coincident with the longitudinal axis of instrument (510), a practitioner may easily access either of first and second legs (526a, 526b) regardless of the left-handedness or right-handedness of the practitioner. As shown in FIG. 9, button (526) extends along a plane that is perpendicular to the longitudinal axis of shaft assembly (130). However, in other examples, button (526) may extend along a plane that is obliquely oriented relative to the longitudinal axis of shaft assembly (130).

Figure 10:
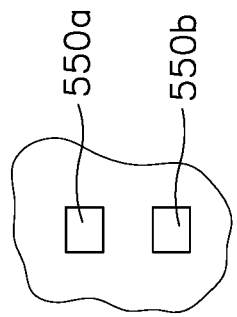
FIG. 10 depicts a front elevational view of one exemplary switch layout that may be associated with the activation button of FIG. 9.

FIG. 10 shows one example of a layout of switches (550a, 550b) that may be associated with button (526). In particular, switches (550a, 550b) may be laid under button (526) such that at least one switch (550a, 550b) will be closed when button (526) is actuated. In some such versions, switch (550a) is positioned such that switch (550a) will be closed when at least one of legs (526a, 526c, 526d) or the center of button (526) is actuated; but not when leg (526b) is actuated. Switch (550b) is positioned such that switch (550b) will be closed when at least one of legs (526b, 526c, 526d) or the center of button (526) is actuated; but not when leg (526a) is actuated. It should therefore be understood that if button (526) is not being actuated, then both switches (550a, 550b) are open. If the operator actuates leg (526a), switch (550a) is closed. If the operator actuates leg (526b), switch (550b) is closed. If the operator actuates either leg (526c), leg (526d), or the center of button (526), both switches (550a, 550b) will be closed.

In some versions where the layout of switches (550a, 550b) of FIG. 10 is used, a control logic (e.g., within instrument (510) and/or within generator (116)) is programmed with a control algorithm that provides a power selection in response to closure of a single switch (550a, 550b) and activation in response to closure of both switches (550a, 550b) simultaneously. For instance, an operator may first press either leg (526a) or leg (526b) to close only switch (550*a*) or only switch (550*b*), respectively. If the operator actuates leg (526*a*) and thereby closes only switch (550*a*), the control logic may select a first power level. If the operator actuates leg (526*b*) and thereby closes only switch (550*b*), the control logic may select a second power level. Once the operator has selected a power level by actuating either leg (526*a*) or leg (526*b*), the operator may then actuate either leg (526*c*) or leg (526*d*), thereby closing both switches (550*a*, 550*b*) simultaneously. In response to the simultaneous closure of both switches (550*a*, 550*b*), the control logic may provide activation of the end effector at the selected power level, regardless of whether the operator has actuated leg (526*c*) or leg (526*d*).

Figure 11:
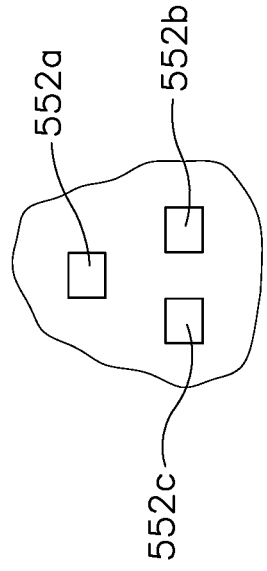
FIG. 11 depicts a front elevational view of another exemplary switch layout that may be associated with the activation button of FIG. 9.

FIG. 11 shows another example of a layout of switches (552*a*, 552*b*, 552*c*) that may be associated with button (526). In particular, switches (552*a*, 552*b*, 552*c*) may be laid under button (526) such that at least one switch (552*a*, 552*b*, 552*c*) will be closed when button (526) is actuated. In some such versions, switch (552*a*) is positioned such that switch (552*a*) will be closed when at least one of legs (526*a*, 526*c*, 526*d*) or the center of button (526) is actuated; but not when leg (526*b*) is actuated. Switch (552*b*) is positioned such that switch (552*b*) will be closed when at least one of legs (526*b*, 526*d*) or the center of button (526) is actuated; but not when legs (526*a*, 526*c*) are actuated. Switch (552*c*) is positioned such that switch (552*c*) will be closed when at least one of legs (526*b*, 526*c*) or the center of button (526) is actuated; but not when legs (526*a*, 526*d*) are actuated. It should therefore be understood that if button (526) is not being actuated, then all switches (552*a*, 552*b*, 552*c*) are open. If the operator actuates leg (526*a*), switch (552*a*) is closed. If the operator actuates leg (526*b*), switches (552*b*, 552*c*) are closed. If the operator actuates leg (526*c*), switches (552*a*, 552*c*) are closed. If the operator actuates leg (526*d*), switches (552*a*, 552*b*) are closed. If the operator actuates the center of button (526), all switches (552*a*, 552*b*, 552*c*) will be closed. Various suitable control algorithms that may be executed in response to various permutations of switch (552*a*, 552*b*, 552*c*) closures will be apparent to those of ordinary skill in the art in view of the teachings herein.

Figure 12:
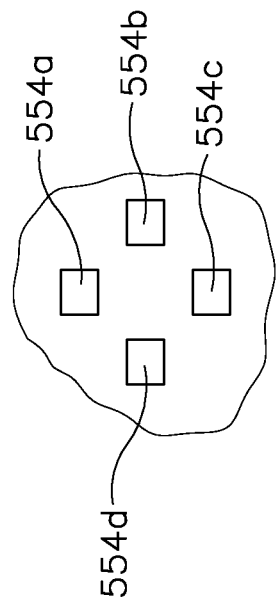
FIG. 12 depicts a front elevational view of another exemplary switch layout that may be associated with the activation button of FIG. 9.

FIG. 12 shows another example of a layout of switches (554*a*, 554*b*, 554*c*, 554*d*) that may be associated with button (526). In particular, switches (554*a*, 554*b*, 554*c*, 554*d*) may be laid under button (526) such that at least one switch (554*a*, 554*b*, 554*c*, 554*d*) will be closed when button (526) is actuated. In some such versions, switch (554*a*) is positioned such that switch (554*a*) will be closed when leg (526*a*) or the center of button (526) is actuated. Switch (554*b*) is positioned such that switch (554*b*) will be closed when leg (526*d*) or the center of button (526) is actuated. Switch (554*c*) is positioned such that switch (554*c*) will be closed when leg (526*c*) or the center of button (526) is actuated. Switch (554*d*) is positioned such that switch (554*d*) will be closed when leg (526*b*) or the center of button (526) is actuated. If button (526) is not being actuated, then all switches (554*a*, 554*b*, 554*c*, 554*d*) are open.

Continuing with the example of FIG. 12, if the operator actuates leg (526*a*), switch (554*a*) is closed. If the operator actuates leg (526*b*), switch (554*b*) is closed. If the operator actuates leg (526*c*), switch (554*c*) is closed. If the operator actuates leg (526*d*), switch (554*d*) is closed. If the operator actuates legs (526*a*, 526*d*) simultaneously, switches (554*a*, 554*b*) are closed. If the operator actuates legs (526*d*, 526*b*) simultaneously, switches (554*b*, 554*c*) are closed. If the operator actuates legs (526*b*, 526*c*) simultaneously, switches (554*c*, 554*d*) are closed. If the operator actuates legs (526*c*, 526*a*) simultaneously, switches (554*d*, 554*a*) are closed. If the operator actuates the center of button (526), all switches (554*a*, 554*b*, 554*c*, 554*d*) will be closed. Various suitable control algorithms that may be executed in response to various permutations of switch (554*a*, 554*b*, 554*c*, 554*d*) closures will be apparent to those of ordinary skill in the art in view of the teachings herein.

Other suitable configurations of buttons and switches, and power levels and operating modes associated therewith, will be apparent to persons skilled in the art in view of the teachings herein.

F. Surgical Instrument with Dual Stage Switch

Figure 13:
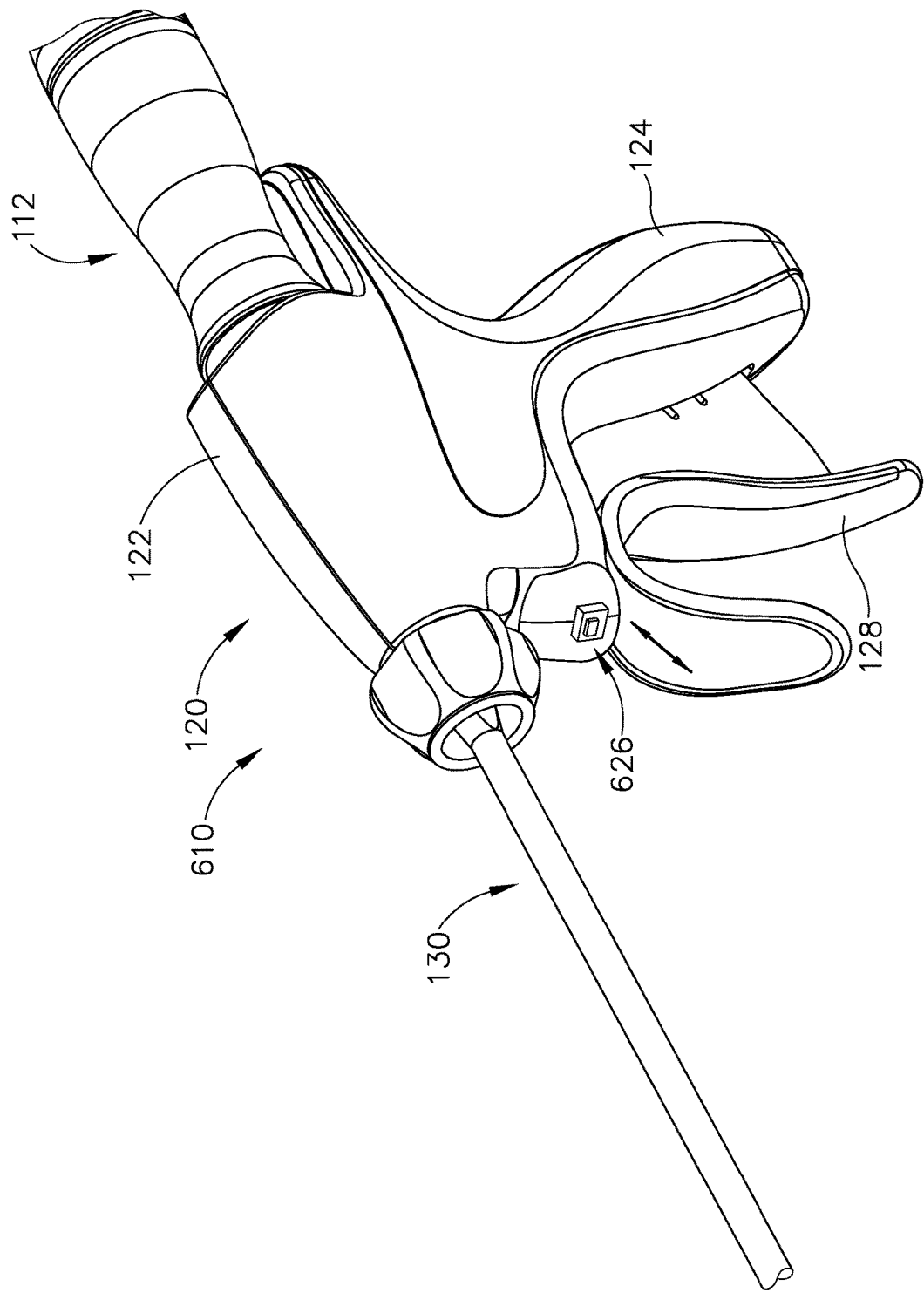
FIG. 13 depicts a perspective view of another exemplary surgical instrument, including another exemplary alternative activation button.

FIG. 13 shows an exemplary alternative surgical instrument (610) that is configured to operate substantially similar to surgical instrument (110). Therefore, identical or similar structures are labeled with like reference numerals without further explanation below. It will be understood that although an end effector is not shown in FIG. 13, instrument (510) includes an end effector just like end effector (140). It will be further understood that transducer (112) may be in communication with a generator (12, 116) via cable (14). As shown, instrument (610) includes a dual stage switch (626) comprising a first switch (626*a*) and a second switch (626*b*). Switches (626*a*, 626*b*) are coaxially aligned with each other in this example. As discussed in further detail below, actuating or depressing first switch (626*a*) activates transducer (112) to operate in a first operating mode, while depressing both first and second switches (626*a*, 626*b*) together activates transducer (112) to operate in a second operating mode.

As shown, first switch (626*a*) defines a central opening (628) extending between a distal end (630) and a proximal end (632) of the first switch (626*a*). First switch (626*a*) includes a proximal flange (634). Second switch (626*a*) includes a rod member (636) that is shaped and configured to be received in opening (628) of first switch (626*a*). Second switch (626*b*) includes a proximal flange (638) extending radially outwardly from rod member (636). As shown, opening (628) has a generally square cross-sectional shape while rod member (636) also has a generally square cross-sectional shape. In other examples, however, portions of first and second switches (626*a*, 626*b*), including opening (628) and rod (636) may have any other suitable cross-sectional shapes (e.g., circular, etc.).

In the present example, first and second switches (626*a*, 626*b*) are co-located such that an operator may depress first and second switches (626*a*, 626*b*) simultaneously if desired. More particularly, first and second switches (626*a*, 626*b*) are oriented coaxially relative to one another such that first and second switches extend along an axis that is parallel to, but offset from, the longitudinal axis of shaft assembly (130). In other examples, first and second switches (626*a*, 626*b*) may be co-located but not necessarily coaxial with one another. In the example shown, first and second switches (626*a*, 626*b*) are each in communication with a respective resilient member (640*a*, 640*b*) that each bias the corresponding first and second switches (626*a*, 626*b*) distally relative to housing (122) (e.g., toward end effector (40)).

Figure 14A:
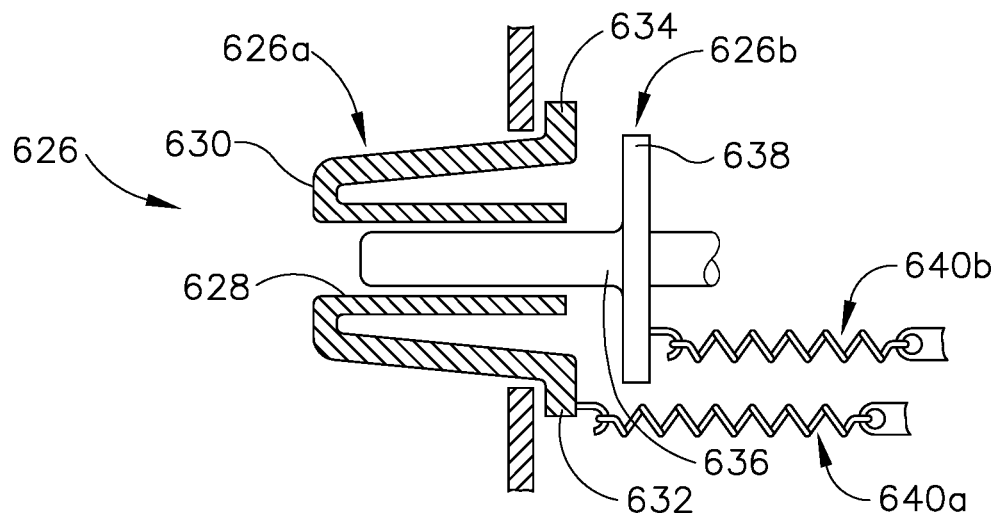
FIG. 14A depicts a cross-sectional side view of the activation button of FIG. 12, showing the button in a non-activating state.
Figure 14B:
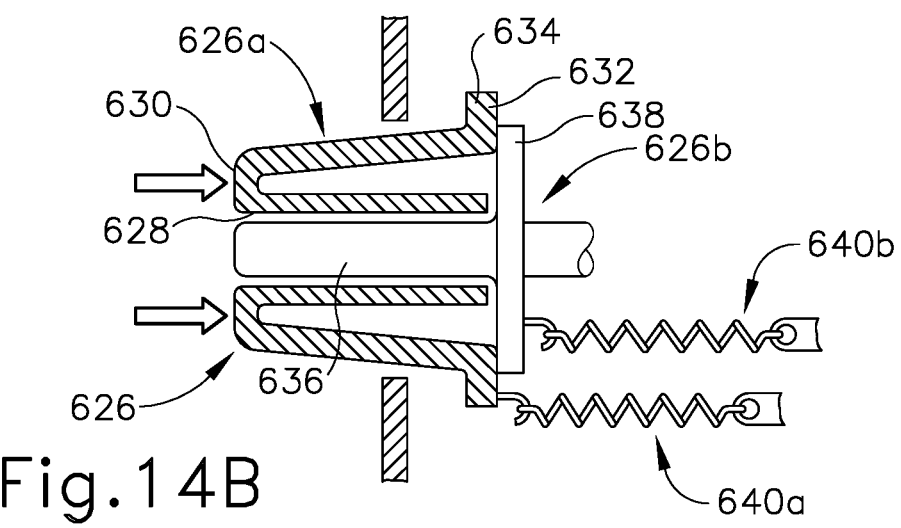
FIG. 14B depicts a cross-sectional side view of the activation button of FIG. 12, showing the button in a first activating state.
Figure 14C:
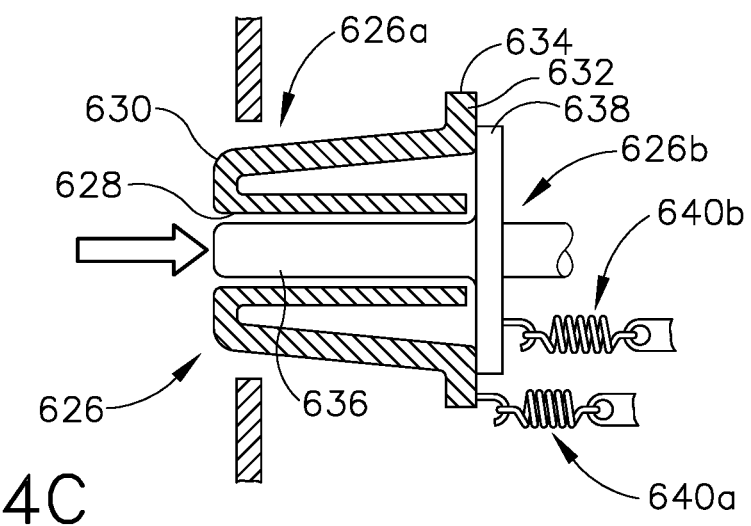
FIG. 14C depicts a cross-sectional side view of the activation button of FIG. 12, showing the button in a second activating state.

Switch (626) of the present example is movable among three positions to switch instrument (610) among various operating modes, as discussed in further detail below. In the first position of switch (626) as shown in FIG. 14A, both first and second switches (626*a*, 626*b*) are in distally extended position relative to housing (122). Switches (626*a*, 626*b*) are configured such that rod member (636) is recessed within opening (628), with rod member (636) being proximal to distal end (630), in the first position. In the second position, as shown in FIG. 14B, second switch (626*b*) remains substantially in the same position as shown in FIG. 14A and first switch (626a) has been actuated or depressed proximally after providing a sufficient force to overcome the distal bias of first resilient member (640a). It should therefore be understood that first switch (626a) is configured to translate proximally through a first range of motion while second switch (626b) remains stationary. As shown, proximal flange (634) of first switch (626a) abuts proximal flange (638) of second switch (626b) in the second position such that further proximal movement of first switch (626a) will drive second switch (626b) proximally. In some examples, second resilient member (640b) is configured to resist further proximal movement of first switch (626a) absent a sufficient additional force by a user on the switch (626).

As shown in FIG. 14B, in the second position, a distal portion (642) of rod member (636) extends slightly distally of the distal end (630) of first switch (626a). Therefore, due to multiple features of switch (626), upon depressing the first switch (626a) relative to second switch (626b), an operator is provided with further tactile feedback that informs the operator of the position of switch (626) (and thus the operating mode of instrument (610), discussed further below). First, the operator's finger may contact the distal portion (642) of rod member (636) and feel that distal portion (642) of rod member (636) has extended distally of distal end (630). Moreover, in some instances the operator may feel the resistance preventing first and second switches (626a, 626b) from moving further proximally due to the bias from resilient members (640a, 640b). Additionally or alternatively, the operator may sense or feel tactile feedback from flanges (634, 638) contacting one another.

In order to move switch (626) to the third position as shown in FIG. 13C, the operator may further depress or actuate proximally both of the first and second switches (626a, 626b) together. As discussed above, the operator depresses first and second switches (626a, 626b) with a sufficient force to overcome the distal resilient bias of resilient members (640a, 640b) in order to transition switch (626) to the third position. In some examples, instrument (610) may include another positive stop feature that prevents the operator from retracting first and second switches (626a, 626b) further proximally (e.g. proximally past the third position shown in FIG. 13C), providing another tactile feedback feature that informs the operator of the position of switch (626).

In the present example, when switch (626) is in the first position, transducer (112) and blade (160) are in a non-activated state. When switch (626) is in the second position, transducer (112) and blade (160) are activated in a first operating mode or power level. The first operating mode may be any of the operating modes discussed herein or other operating modes that will be apparent to persons skilled in the art in view of the teachings herein. For example, the first operating mode may be the "seal" mode discussed above. When switch (626) is in the third position, transducer (112) and blade (160) are activated in a second operating mode or power level. The second operating mode may be any of the operating modes discussed herein or other operating modes that will be apparent to persons skilled in the art in view of the teachings herein. For example, the second operating mode may be the "cut and seal" mode discussed above. Other suitable operating modes and configurations of switch (626) will be apparent to persons skilled in the art in view of the teachings herein.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body; (b) an actuation assembly, wherein the actuation assembly comprises an activation member, wherein the activation member is operable to move in a first direction to select a mode of operation; (c) a shaft assembly extending distally from the body, wherein the shaft assembly defines a longitudinal axis, wherein the shaft assembly comprises an acoustic waveguide; and (d) an end effector comprising an ultrasonic blade, wherein the ultrasonic blade is in acoustic communication with the acoustic waveguide, wherein the activation member is operable to move in a second direction to activate the end effector in a mode of operation selected by movement of the activation member in the first direction.

Example 2

The ultrasonic instrument of Example 1, wherein the end effector is configured to be activated in a first activation mode in response to movement of the activation member in the second direction when the activation member is in a first position, wherein the end effector is configured to be activated in a second activation mode in response to movement of the activation member in the second direction when the activation member is in a second position.

Example 3

The ultrasonic instrument of any one or more of Examples 1 through 2, wherein the activation member comprises a rotatable wheel, wherein the rotatable wheel is configured to rotate about a rotational axis that is perpendicular to the longitudinal axis of the shaft assembly to select a mode of operation, wherein the second direction is transverse to the rotational axis.

Example 4

The ultrasonic instrument of any one or more of Examples 1 through 3, wherein the activation member comprises a button, wherein the button is movable laterally in the first direction.

Example 5

The ultrasonic instrument of Example 4, wherein the button is pivotable laterally in the first direction about a pivot axis that is perpendicular to the longitudinal axis of the shaft assembly.

Example 6

The ultrasonic instrument of Example 5, wherein the pivotable button is configured to pivot in the first direction between a first position, a second position, and a third position, wherein the second position is between the first and third positions.

Example 7

The ultrasonic instrument of Example 6, wherein the pivotable button is resiliently biased to the second position.

Example 8

The ultrasonic instrument of any one or more of Examples 6 through 7, wherein the pivotable button is inoperable to activate the end effector when the pivotable button is in the second position.

Example 9

The ultrasonic instrument of any one or more of Examples 1 through 8, wherein the activation member is configured to select between a first mode of operation and a second mode of operation, wherein the end effector is configured to apply ultrasonic energy to tissue at a first power level in the first mode of operation, wherein the activation member is configured to apply ultrasonic energy to tissue at a second power level in the second mode of operation.

Example 10

The ultrasonic instrument of any one or more of Examples 1 through 9, wherein the activation member is configured to select between a first mode of operation and a second mode of operation, wherein the end effector is configured to apply ultrasonic energy to tissue in the first mode of operation, wherein the activation member is configured to apply RF energy to tissue in the second mode of operation.

Example 11

The ultrasonic instrument of any one or more of Examples 1 through 10, wherein the body is configured to be grasped by a hand of an operator.

Example 12

The ultrasonic instrument of Example 11, further comprising a sensor, wherein the sensor is configured to sense whether the body is grasped by a right hand or a left hand of an operator.

Example 13

The ultrasonic instrument of Example 12, further comprising a controller in communication with the sensor, wherein the actuation assembly further comprises a first lateral actuator and a second lateral actuator, wherein the first and second lateral actuators are on opposite lateral sides of the body, wherein the controller is operable to vary functionality of the first and second lateral actuators based on data from the sensor indicating whether the body is grasped by a right hand or a left hand of an operator.

Example 14

The ultrasonic instrument of Example 13, wherein the activation member is operable to activate the end effector to apply ultrasonic energy to tissue via the ultrasonic blade, wherein the first lateral actuator or the second lateral actuator is operable to activate the end effector to apply RF electrosurgical energy to tissue.

Example 15

The ultrasonic instrument of any one or more of Examples 1 through 14, further comprising a visual indicator on the body, wherein the visual indicator is configured to provide visual feedback indicating a mode of operation selected through movement of the activation member in the first direction.

Example 16

An ultrasonic instrument comprising: (a) a body; (b) a button assembly, wherein the button assembly comprises: (i) a first button member defining an opening and a distal face, and (ii) a second button member positioned within the opening of the first button member; (c) a shaft assembly extending distally from the body; and (d) an end effector positioned at a distal end of the shaft assembly, wherein the end effector is operable to apply one or both of ultrasonic energy or RF electrosurgical energy to tissue; wherein the first button member is configured to translate through a first range of motion relative to the body to activate the end effector in a first mode of operation, wherein the second button member is configured to remain stationary relative to the body as the first button member translates through the first range of motion; wherein the first button member is configured to translate through a second range of motion relative to the body to activate the end effector in a second mode of operation, wherein the second button member is configured to translate with the first button member relative to the body as the first button member translates through the second range of motion.

Example 17

The ultrasonic instrument of Example 16, wherein the second button member has a distal end, wherein the distal end is recessed within the opening and relative to the distal face of the first button member until the first button member translates through the first range of motion.

Example 18

The ultrasonic instrument of any one or more of Examples 16 through 17, wherein the first button member has a proximal flange, wherein the second button member has a proximal flange, wherein the proximal flange of the first button member is configured to engage the proximal flange of the second button member upon completion of the first range of motion by the first button member.

Example 19

An ultrasonic instrument comprising: (a) a body; (b) an actuation assembly, wherein the actuation assembly comprises an activation member, wherein the activation member is operable to move along a range of motion relative to the body; (c) a shaft assembly extending distally from the body, wherein the shaft assembly defines a longitudinal axis, wherein the shaft assembly comprises an acoustic waveguide; and (d) an end effector comprising an ultrasonic blade, wherein the ultrasonic blade is in acoustic communication with the acoustic waveguide, wherein the activation member is operable to activate the ultrasonic blade at a progressively increasing power level along a continuous range of power levels based on the position of the activation member along the range of motion relative to the body.

Example 20

The ultrasonic instrument of Example 19, wherein the activation member is operable to activate the ultrasonic blade at a progressively increasing power level along a continuous range of power levels that is proportional to the position of the activation member along the range of motion relative to the body.

IV. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector including an activation feature;
   (b) a shaft assembly, wherein the end effector distally extends from the shaft assembly; and
   (c) a switch operatively connected to the activation feature of the end effector and configured to selectively move from a first state through a second state to a third state, wherein the switch is configured to direct operation of the activation feature according to a first mode, a second mode, and a third mode respectively in the first, second and third states, wherein the switch includes a first switch portion and a second switch portion, wherein the first switch portion is configured to actuate relative to the second switch portion from the first state to the second state for the second mode of operation, and wherein the first and second switch portions are co-located such that the first switch portion is configured to abut against the second switch portion to actuate simultaneously together from the second state to the third state for the third mode of operation, wherein the activation feature is deactivated in the first mode, wherein the activation feature is activated with a first power level in the second mode, wherein the activation feature is activated with a different, second power level in the third mode.

2. The surgical instrument of claim 1, further comprising a body assembly, wherein the switch is positioned on the body assembly, and wherein the first switch portion is configured to actuate relative to the body assembly and the second switch portion from the first state to the second state for the second mode of operation, and wherein the first and second switch portions are configured to actuate simultaneously together relative to the body assembly from the second state to the third state for the third mode of operation.

3. The surgical instrument of claim 2, wherein the second switch portion is configured to remain stationary relative to the body assembly from the first state to the second state for the second mode of operation.

4. The surgical instrument of claim 2, wherein the shaft assembly distally extends from the body assembly.

5. The surgical instrument of claim 1, wherein the switch is configured to selectively move in a first direction from the first state through the second state to the third state, wherein the first switch portion is configured to actuate in the first direction relative to the second switch portion from the first state to the second state for the second mode of operation, and wherein the first and second switch portions are configured to actuate simultaneously together in the first direction from the second state to the third state for the third mode of operation.

6. The surgical instrument of claim 5, wherein the first direction is a proximal direction.

7. The surgical instrument of claim 1, wherein each of the first and second switch portions are configured to remain unactuated in the first state for the first mode of operation.

8. The surgical instrument of claim 7, wherein each of the first and second switch portions are biased toward the first state.

9. The surgical instrument of claim 1, wherein the first switch portion includes a first switch member, wherein the second switch portion includes a second switch member, and wherein the second switch member is positioned at least partially within the first switch member.

10. The surgical instrument of claim 9, wherein the first and second switch members extend along a switch axis, and wherein the first switch member surrounds the second switch member about the switch axis.

11. The surgical instrument of claim 1, wherein the switch is configured to generate a first tactile feedback upon selective movement from the first state to the second state, wherein the switch is configured to generate a second tactile feedback upon selective movement from the second state to the third state, and wherein the second tactile feedback is different than the first tactile feedback.

12. The surgical instrument of claim 11, wherein the first tactile feedback includes a first resistance to selective movement, wherein the second tactile feedback includes a second resistance to selective movement, and wherein the second resistance is greater than the first resistance.

13. The surgical instrument of claim 1, wherein the end effector includes an ultrasonic blade, wherein the shaft assembly includes an acoustic waveguide, and wherein the acoustic waveguide is in acoustic communication with the ultrasonic blade.

14. A surgical instrument, comprising:
(a) an end effector including an activation feature;
(b) a shaft assembly, wherein the end effector distally extends from the shaft assembly; and
(c) a switch operatively connected to the activation feature of the end effector and configured to selectively move from a first state through a second state to a third state, wherein the switch is configured to direct operation of the activation feature according to a first mode, a second mode, and a third mode respectively in the first, second and third states, wherein the switch includes a first switch portion and a second switch portion, wherein the first switch portion is configured to actuate relative to the second switch portion from the first state to the second state for the second mode of operation, and wherein the first and second switch portions are configured to actuate simultaneously together from the second state to the third state for the third mode of operation,
wherein the first switch portion includes a first switch member, wherein the second switch portion includes a second switch member, and wherein the second switch member is positioned at least partially within the first switch member.

15. The surgical instrument of claim 14, wherein each of the first and second switch members extend along a switch axis.

16. The surgical instrument of claim 15, wherein the first switch member surrounds the second switch member about the switch axis.

17. A surgical instrument, comprising:
(a) an end effector including an ultrasonic blade;
(b) a shaft assembly including an acoustic waveguide in acoustic communication with the ultrasonic blade, wherein the end effector distally extends from the shaft assembly; and
(c) a switch operatively connected to the ultrasonic blade of the end effector and configured to selectively move from a first state through a second state to a third state, wherein the switch is configured to direct operation of the ultrasonic blade according to a first mode, a second mode, and a third mode respectively in the first, second and third states, wherein the switch includes a first switch portion and a second switch portion, wherein the first switch portion is configured to actuate relative to the second switch portion from the first state to the second state for the second mode of operation, and wherein the first and second switch portions are configured to actuate simultaneously together from the second state to the third state for the third mode of operation,
wherein the ultrasonic blade is deactivated in the first mode, wherein the ultrasonic blade is activated with a first power level in the second mode, wherein the ultrasonic blade is activated with a different, second power level in the third mode.

18. The surgical instrument of claim 17, wherein the acoustic waveguide extends along a longitudinal axis, wherein each of the first and second switch portions extend and actuate along a switch axis, and wherein the switch axis is parallel to and offset from the longitudinal axis.

* * * * *